United States Patent
Hung

(10) Patent No.: US 10,081,737 B2
(45) Date of Patent: Sep. 25, 2018

(54) METHOD FOR PRODUCING CURING AGENT OF COATING AND ITS APPLICATION ON COATING

(71) Applicant: SHANGHAI YAO HE BIOCHEMICAL TECHNOLOGY CO., LTD., Shanghai (CN)

(72) Inventor: Shun-Ming Hung, Nantou (TW)

(73) Assignee: SHANGHAI YAO HE BIOCHEMICAL TECHNOLOGY CO., LTD., Shanghai (CN)

( * ) Notice: Subject to any disclaimer, the term of this patent is extended or adjusted under 35 U.S.C. 154(b) by 0 days.

(21) Appl. No.: 15/598,198

(22) Filed: May 17, 2017

(65) Prior Publication Data
US 2017/0335134 A1 Nov. 23, 2017

(30) Foreign Application Priority Data
May 23, 2016 (CN) .......................... 2016 1 0345178

(51) Int. Cl.
| | | |
|---|---|---|
| C09D 167/00 | (2006.01) |
| C07C 67/00 | (2006.01) |
| C07C 67/10 | (2006.01) |
| C07D 301/12 | (2006.01) |
| C09D 5/03 | (2006.01) |
| C09D 5/00 | (2006.01) |

(52) U.S. Cl.
CPC ............ *C09D 167/00* (2013.01); *C07C 67/10* (2013.01); *C07D 301/12* (2013.01); *C09D 5/00* (2013.01); *C09D 5/03* (2013.01)

(58) Field of Classification Search
CPC ...... C09D 167/00; C09D 301/12; C09D 5/03; C09D 5/00; C07C 67/10
USPC ....................................................... 524/601
See application file for complete search history.

(56) References Cited

U.S. PATENT DOCUMENTS

| | | | | |
|---|---|---|---|---|
| 3,859,314 A | * | 1/1975 | Dukes .................. | C07D 303/16 549/515 |
| 4,667,044 A | * | 5/1987 | Nees .................... | C07D 303/16 549/539 |
| 5,294,683 A | * | 3/1994 | Cotting ................ | C07D 303/22 313/318.05 |

* cited by examiner

*Primary Examiner* — Michael Bernshteyn
(74) *Attorney, Agent, or Firm* — Pai Patent & Trademark Law Firm; Chao-Chang David Pai

(57) ABSTRACT

The curing agent for coatings includes at least 1,3,5-triglycidyl benzenetricarboxylate and 1,3,5-diglycidyl benzenetricarboxylate. To produce the curing agent, 1,3,5-benzenetricarboxylic acid reacts with a base and chloropropene to produce triallyl benzene-1,3,5-tricarboxylate. Then the triallyl benzene-1,3,5-tricarboxylate reacts with a surfactant, hydrogen peroxide and a catalyst to produce 1,3,5-triglycidyl benzenetricarboxylate and/or 1,3,5-diglycidyl benzenetricarboxylate. The 1,3,5-triglycidyl benzenetricarboxylate can be applied to coatings as a curing agent.

16 Claims, No Drawings

METHOD FOR PRODUCING CURING AGENT OF COATING AND ITS APPLICATION ON COATING

BACKGROUND OF THE INVENTION

1. Field of the Invention

The present invention relates to a method for producing a curing agent of coatings and its application on coatings, and more particularly to a curing agent of coatings including 1,3,5-triglycidyl benzenetricarboxylate and its application on the polyester powder coating.

2. Related Prior Arts

Recently, powder coatings have been fast developed because of their relatively less environment pollution. As an important composition of the polyester powder coating, curing agents such as 1,3,5-Triglycidyl isocyanurate (TGIC) or N,N,N',N'-Tetrakis (2-hydroxyethyl)adipamide (HAA) are usually added therein.

TGIC was developed earlier and performs good functions but may cause irritation to skin and eyes. On 1991, TGIC was further found as a carcinogenic and mutagenic substance and thus forbidden in many countries. HAA without irritation and carcinogenicity therefore was intended to replace TGIC as the curing agent of weather-resistant powder coatings. However, HAA cannot perform as well as TGIC in some characteristics and fields of application. Therefore, TGIC is still used in some areas outside Europe.

To overcome the above problems, the inventors carefully researched 1,3,5-glycidyl benzenetricarboxylate and found that it functions as well as TGIC but without disadvantages thereof. Compared to HAA, 1,3,5-glycidyl benzenetricarboxylate also performs better in terms of properties such as gloss, anti-corrosion, gloss retention, solvent resistance and high temperature resistance. Accordingly, 1,3,5-glycidyl benzenetricarboxylate can serve as a curing agent of powder coatings better than TGIC and HAA.

Traditionally, 1,3,5-triglycidyl benzenetricarboxylate is produced by reacting 1,3,5-benzenetricarboxylic acid with epichlorohydrin (ECH). This process has the following disadvantages:

1. ECH is an irritant, toxic and carcinogenic substance.

2. Chlorine ions remaining in the product are unfavorable to electrical materials and therefore applications thereof are restricted.

3. The yield is lower than 80%.

Therefore, it is necessary to develop a better curing agent and a manufacturing process without the above disadvantages.

SUMMARY OF THE INVENTION

The object of the present invention is to provide a method for producing a curing agent of coatings, which is more environmental friendly and has a higher yield.

In this invention, the curing agent of coatings includes at least 1,3,5-triglycidyl benzenetricarboxylate having the structural formula (B)

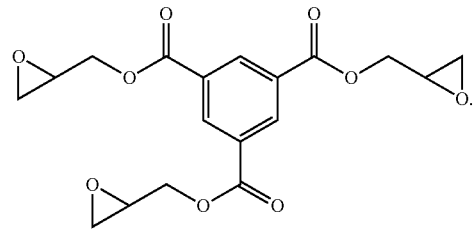

The method for producing the curing agent of coatings includes the following steps:

(1) mixing 1,3,5-benzenetricarboxylic acid, a base and chloropropene in a solvent to proceed with a reaction at 40-80° C. and generate triallyl benzene-1,3,5-tricarboxylate (product A), wherein the base and 1,3,5-benzenetricarboxylic acid have an equivalent ratio of 2.0-6.0, and the chloropropene and 1,3,5-benzenetricarboxylic acid have an equivalent ratio of 2-5; and (2) mixing the product A, a surfactant and hydrogen peroxide in a water solution of a first catalyst to proceed with a reaction at 50-80° C. and generate the curing agent of the coating including 1,3,5-triglycidyl benzenetricarboxylate having the structural formula (B)

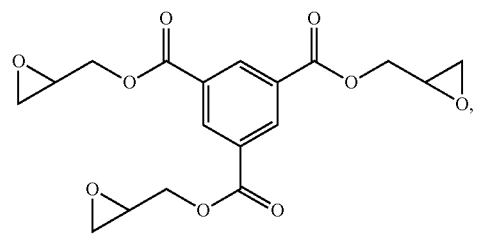

and/or
1,3,5-diglycidyl benzenetricarboxylate having the structural formula (C)

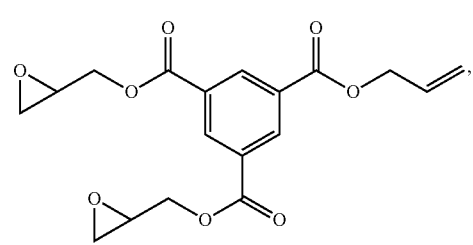

wherein the surfactant and triallyl benzene-1,3,5-tricarboxylate have a weight ratio of 0.01-0.1, the catalyst and triallyl benzene-1,3,5-tricarboxylate have a weight ratio of 0.05-0.15, and hydrogen peroxide and triallyl benzene-1,3,5-tricarboxylate have an equivalent ratio of 3.5-5.0.

The base of the step (1) is preferably triethylamine, and the solvent can be 1,2-dichloroethane, N,N-dimethylformide, petroleum ether or toluene. The equivalent of chloropropene and 1,3,5-benzenetricarboxylic acid is preferably ranging 2.5-4.5, and the reaction is preferably controlled at 50-65° C.

The first catalyst of the step (2) is preferably sodium tungstate or derivatives thereof, and the pH is preferably 2.0-5.0. The surfactant can be tetrabutylammonium bromide (TBAB), benzyltriethylammonium chloride (BTEAC), benzyltrimethylammonium chloride (BTMAC) or N-Methyl-N,N,N-trioctylammonium chloride (Aliquat 336). The reaction is preferably controlled at 60-65° C. for 12-24 hours. The weight ratio of the surfactant and the product A is preferably 0.03-0.05, and the weight ratio of the catalyst and the product A is preferably 0.05-0.10.

Furthermore, a step can be carried out after the step (2):

(2a) adding a second catalyst and hydrogen gas to proceed with a reaction and generate 1,3,5-diglycidyl benzenetricarboxylate having the structural formula (D)

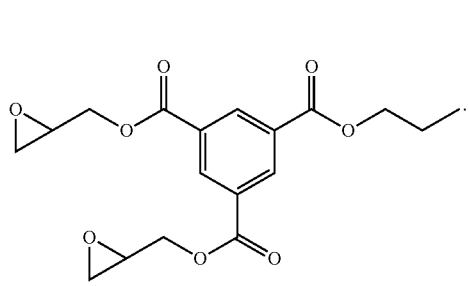

The second catalyst of the step (2a) is preferably Pd/C (palladium on carbon), and the reaction is preferably controlled at 20-40° C.

According to the above method, the product including 1,3,5-triglycidyl benzenetricarboxylate (B) and 1,3,5-diglycidyl benzenetricarboxylate (C) or (D) can be obtained, wherein the product (B) preferably has an amount of 40-99 wt %. The product is suitable for a curing agent of polyester powder coatings, for example, the carboxyl-terminated polyester powder coating.

In the present invention, no carcinogenic material is used. Hydrogen peroxide is provided as an oxygen source to generate harmless water. The yield of the curing agent is higher than 90%. Both 1,3,5-triglycidyl benzenetricarboxylate and 1,3,5-diglycidyl benzenetricarboxylate can react with the polyester resin. When the product contains 1,3,5-diglycidyl benzenetricarboxylate in an amount of about 20%, the best conversion 97% and yield 92% are achieved. Tests on the coating films including the product show properties as good as if TGIC is used. The product containing no chlorine ions is also suitable for electrical materials.

DETAILED DESCRIPTION OF THE PREFERRED EMBODIMENTS

The detailed procedures and reactions for producing the curing agent of the coating are as follows:

(1) Producing triallyl benzene-1,3,5-tricarboxylate

A four-necked flask is set with a mechanical stirrer, a condenser and a thermometer. Into the flask, the solvent 1,2-dichloroethane (6.3 equiv) and triethylamine (3.1 equiv) are added and then followed by 1,3,5-benzenetricarboxylic acid (1.0 equiv). When the mixture is heated to 60° C., chloropropene (3.2 equiv) is added therein. The reaction is controlled at about 65° C. with stirring for 3 hours. The chemical equation (I) illustrates this process:

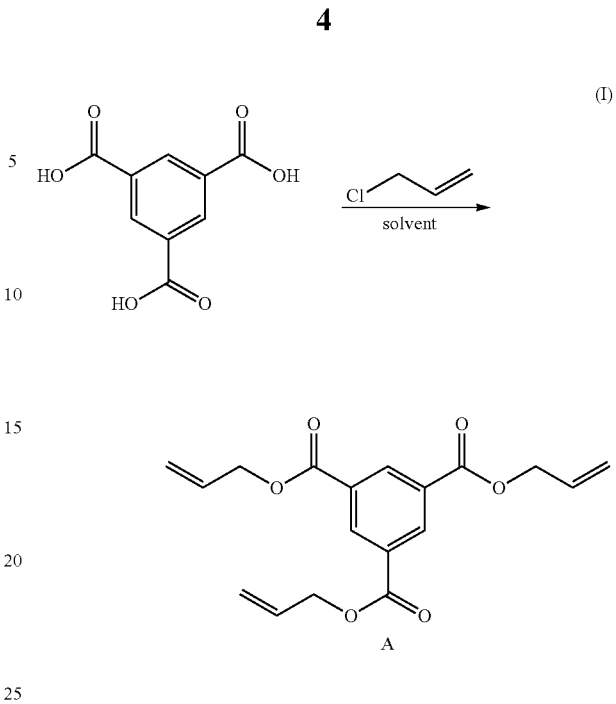

When the reactants remain less than 1%, the reaction is completed. The solvent is vaporized and collected, and 1,2-dichloroethane is added therein. The solution is cooled to about 50° C. and washed with water in an amount of 2-3 times thereof. The solution is then divided into layers wherein the organic layer containing triallyl benzene-1,3,5-tricarboxylate (A) is collected. Purity of the product A is more than 98.0 wt %.

(2) Producing the curing agent APLUS101

Into the water solution of the catalyst (sodium tungstate) with pH 2.5, the solution of triallyl benzene-1,3,5-tricarboxylate (1.0 equiv), the surfactant (tetrabutylammonium bromide (TBAB) and hydrogen peroxide (4.5 equiv) are added. The surfactant and the product A have a weight ratio of 0.03, the catalyst and the product A have a weight ratio of 0.05. The reaction is controlled at 60° C. for 18 hours. The equation (II) illustrates this process:

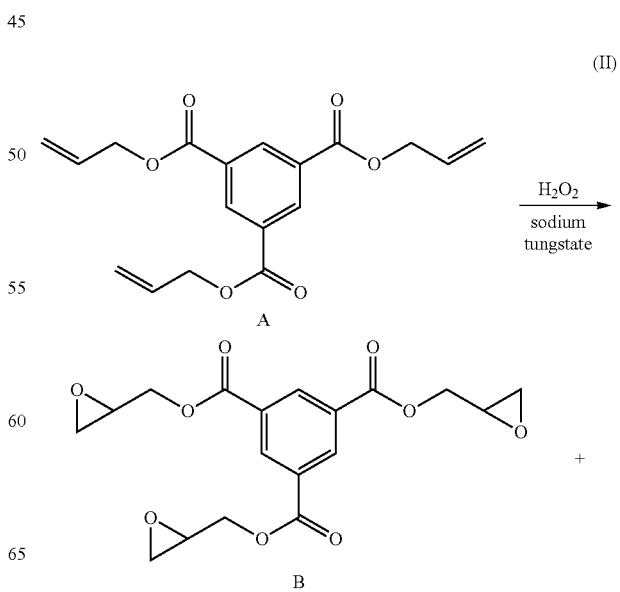

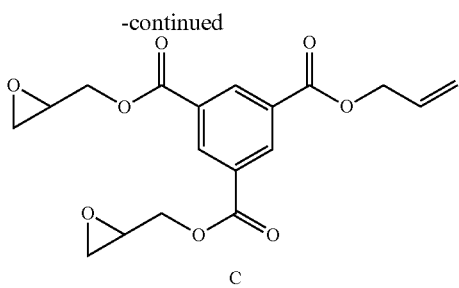

C

When the reaction is completed, the solvent is added to form layers. The organic layer is collected and cooled for crystallization. By means of filtration, the white crystal composition (APLUS101) of 1,3,5-triglycidyl benzenetricarboxylate (B, 80 wt %) and 1,3,5-diglycidyl benzenetricarboxylate (C, 20 wt %) are obtained.

(2a) Producing the Curing Agent APLUS102

Into the collected organic layer of the step (2), Pd/C (1%) is added. The reaction is caused to proceed at 25° C. by delivering hydrogen gas into the reactor, and then 1,3,5-diglycidyl benzenetricarboxylate (C) is converted to 1,3,5-diglycidyl benzenetricarboxylate (D). The equation (III) illustrates such conversion:

(III)

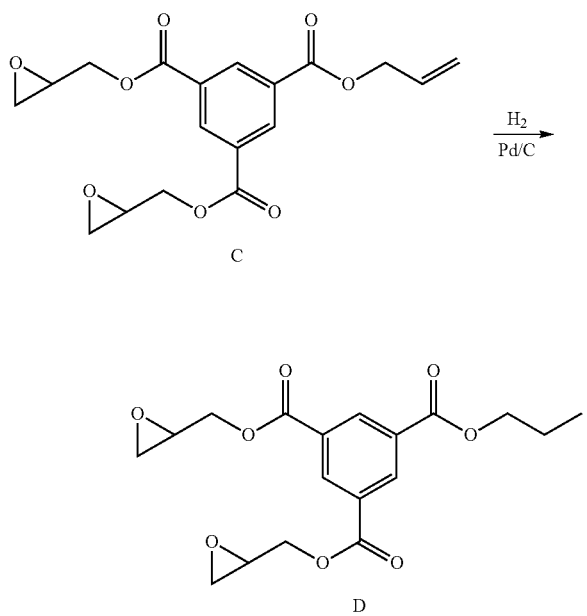

After the reaction is completed, the mixture is filtered to obtain the white solid composition (APLUS102) of 1,3,5-triglycidyl benzenetricarboxylate (B, 80 wt %) and 1,3,5-diglycidyl benzenetricarboxylate (D, 20 wt %).

Application of the Product on the Polyester Powder Coating

To verify properties of the product of the invention, APLUS101, APLUS102, HAA and TGIC are individually mixed with the polyester powder and additives. These curing agents are added in amounts of 2-8 wt % of the polyester powder coatings. The contents of the polyester powder coatings are listed in Table 1.

TABLE 1

| | The curing agents | | | |
|---|---|---|---|---|
| Composition | HAA | TGIC | APLUS101 | APLUS102 |
| Polyester resin A | — | 60 | 60 | 60 |
| Polyester resin B | 60 | — | — | — |
| The curing agent | 2.5 | 4.5 | 4.5 | 4.5 |
| CS-12 | 0.5 | 0.5 | 0.5 | 0.5 |
| Benzoin | 0.3 | 0.3 | 0.3 | 0.3 |
| Titanium dioxide | 26.0 | 26.0 | 26.0 | 26.0 |
| The leveling agent | 1.0 | 1.0 | 1.0 | 1.0 |

The coatings are tested in the form of films and the tests are carried out in the same conditions. The results are as listed in Table 2.

TABLE 2

| | The curing agents | | | |
|---|---|---|---|---|
| Properties | HAA | TGIC | APLUS101 | APLUS102 |
| Gloss of the films | 84.5 | 87.6 | 88.3 | 88.0 |
| Neutral salt-spray tests, 300 h | Slight corrosion | Slight corrosion | No corrosion | No corrosion |
| QUV-A tests, 500 h, gloss retention (%) | 72.7 | 75.8 | 78.5 | 78.1 |
| Flow and leveling (cm) | 3.1 | 3.8 | 4.5 | 4.3 |
| MEK resistance tests, 24 h, gloss loss (%) | 8.16 | 10.25 | 5.86 | 5.93 |
| Heat resistance, 220° C., 15 min* | 1.15 | 0.59 | 0.56 | 0.53 |

*Compared with the color at 200° C., 10 min, less color differences indicate better properties.

As a result, APLUS101 AND APLUS102 perform better than HAA and TGIC. That is, the compositions of the present invention comply with the standards for the curing agents of coatings and can replace HAA and TGIC.

Acute Oral Toxicity Test

Testing facility: Shanghai Research Institute of Chemical Industry Testing Center Test report: No. 1515090029 (2015.09.09)

Test conditions: According to OECD no. 423, acute oral toxicity tests on female mice fed with 2,000 mg/kg, 2,000 mg/kg and 5,000 mg/kg.

Results: No mice were dead, i.e., LD50>5,000 mg/kg (mice).

In summary, the present invention provides advantages as follows:

1. In the manufacturing process, no carcinogenic material is used, and hydrogen peroxide is provided as an oxygen source to generate harmless water.

2. The yield of the curing agent is higher than 90%. Both 1,3,5-triglycidyl benzenetricarboxylate and 1,3,5-diglycidyl benzenetricarboxylate can react with the polyester resin. When the product contains 1,3,5-diglycidyl benzenetricarboxylate in an amount of about 20%, the best conversion 97% and the yield 92% are achieved.

3. The test on the coating including the curing agent shows properties as good as TGIC.

4. The product containing no chlorine ions is also suitable for electrical materials.

The invention claimed is:

1. A method for producing a curing agent of coatings, comprising steps of:
   (1) mixing 1,3,5-benzenetricarboxylic acid, a base and chloropropene in a solvent to proceed with a reaction at 40-80° C. and generate triallyl benzene-1,3,5-tricarboxylate, wherein the base and 1,3,5-benzenetricarboxylic acid have an equivalent ratio of 2.0-6.0, and the chloropropene and 1,3,5-benzenetricarboxylic acid have an equivalent ratio of 2-5;

(2) mixing the triallyl benzene-1,3,5-tricarboxylate, a surfactant and hydrogen peroxide in a water solution of a first catalyst to proceed with a reaction at 50-80° C. and generate the curing agent of coatings including 1,3,5-triglycidyl benzenetricarboxylate having the structural formula (B)

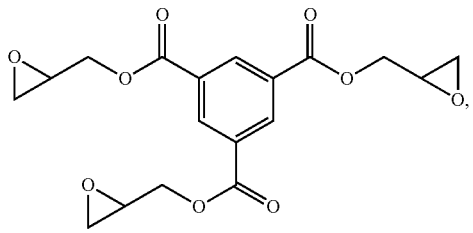

and/or
1,3,5-diglycidyl benzenetricarboxylate having the structural formula (C)

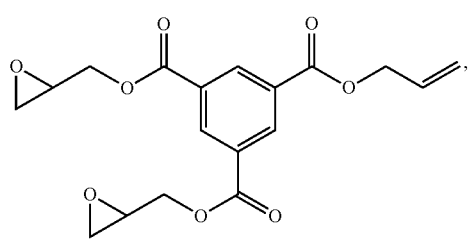

wherein the surfactant and triallyl benzene-1,3,5-tricarboxylate have a weight ratio of 0.01-0.1, the catalyst and triallyl benzene-1,3,5-tricarboxylate have a weight ratio of 0.05-0.15, and the hydrogen peroxide and triallyl benzene-1,3,5-tricarboxylate have an equivalent ratio of 3.5-5.0.

2. The method of claim 1, wherein the base in the step (1) is triethylamine.

3. The method of claim 1, wherein the solvent in the step (1) is 1,2-dichloroethane, N,N-dimethylformide, petroleum ether or toluene.

4. The method of claim 1, wherein the chloropropene and 1,3,5-benzenetricarboxylic acid in the step (1) have an equivalent ratio of 2.5-4.5.

5. The method of claim 1, wherein the reaction in the step (1) is controlled at 50-65° C.

6. The method of claim 1, wherein the surfactant and triallyl benzene-1,3,5-tricarboxylate in the step (2) have a weight ratio of 0.03-0.05.

7. The method of claim 1, wherein the catalyst and triallyl benzene-1,3,5-tricarboxylate in the step (2) have a weight ratio of 0.05-0.10.

8. The method of claim 1, wherein the first catalyst in the step (2) is sodium tungstate or derivatives thereof.

9. The method of claim 1, wherein the surfactant in the step (2) is tetrabutylammonium bromide (TBAB), benzyltriethylammonium chloride (BTEAC), benzyltrimethylammonium chloride (BTMAC) or N-Methyl-N,N,N-trioctylammonium chloride.

10. The method of claim 1, wherein the reaction in the step (2) is controlled at 60-65° C.

11. The method of claim 1, wherein the step (2) is followed by a step:

(2a) adding a second catalyst and hydrogen gas to proceed with a reaction and generate 1,3,5-diglycidyl benzenetricarboxylate having the structural formula (D)

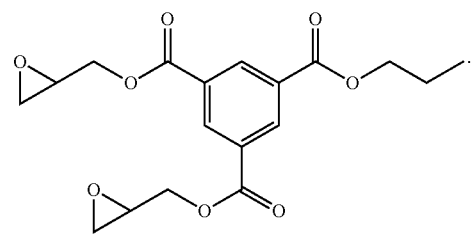

12. The method of claim 11, wherein the second catalyst in the step (2a) is Pd/C (palladium on carbon).

13. A curing agent of coatings, comprising:
1,3,5-triglycidyl benzenetricarboxylate having a structural formula (B)

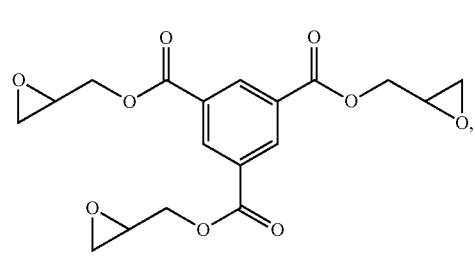

and
1,3,5-diglycidyl benzenetricarboxylate having a structural formula (C) or (D)

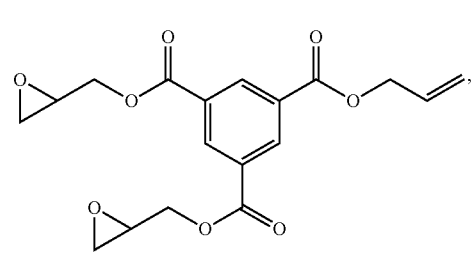

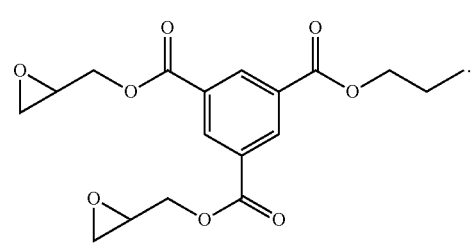

14. The curing agent of the coating of claim 13, wherein 1,3,5-triglycidyl benzenetricarboxylate has an amount of 40-99 wt %.

15. An application on polyester powder coating, wherein the curing agent of coatings of claim 13 is employed.

16. A coating including the curing agent of coatings of claim 13, and a polyester resin.

\* \* \* \* \*